US012594047B2

(12) United States Patent
Flohr et al.

(10) Patent No.: US 12,594,047 B2
(45) Date of Patent: Apr. 7, 2026

(54) CONTRAST AGENT-BASED VASCULAR IMAGING

(71) Applicants: Siemens Healthineers AG, Forchheim (DE); Bayer AG, Leverkusen (DE)

(72) Inventors: Thomas Flohr, Uehlfeld (DE); Bernhard Schmidt, Fuerth (DE); Gregor Jost, Berlin (DE); Hubertus Pietsch, Kleinmachnow (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 618 days.

(21) Appl. No.: 17/779,637

(22) PCT Filed: Nov. 4, 2020

(86) PCT No.: PCT/EP2020/080915
§ 371 (c)(1),
(2) Date: May 25, 2022

(87) PCT Pub. No.: WO2021/104814
PCT Pub. Date: Jun. 3, 2021

(65) Prior Publication Data
US 2023/0000454 A1 Jan. 5, 2023

(30) Foreign Application Priority Data

Nov. 29, 2019 (DE) ..................... 10 2019 218 587.8

(51) Int. Cl.
*A61B 6/00* (2024.01)
*A61B 6/03* (2006.01)
(Continued)

(52) U.S. Cl.
CPC .............. *A61B 6/504* (2013.01); *A61B 6/032* (2013.01); *A61B 6/405* (2013.01); *A61B 6/4241* (2013.01);
(Continued)

(58) Field of Classification Search
CPC ................................ A61B 6/032; A61B 6/504
See application file for complete search history.

(56) References Cited

U.S. PATENT DOCUMENTS

2008/0137803 A1     6/2008  Wu et al.
2009/0086884 A1     4/2009  Krauss
(Continued)

FOREIGN PATENT DOCUMENTS

CN          103356206 A       10/2013
DE      102015212369 A1        1/2016
(Continued)

OTHER PUBLICATIONS

Mongan, John et al; "In Vivo Differentiation of Complementary Contrast Media at Dual-Energy CT"; Radiology; vol. 265; No. 1; pp. 267-272; 2012.

*Primary Examiner* — Joseph M Santos Rodriguez
(74) *Attorney, Agent, or Firm* — Harness, Dickey & Pierce, P. L. C.

(57) ABSTRACT

Embodiments of the present invention relates to an X-ray contrast agent. The X-ray contrast agent has an X-ray absorption the change of which between at least two different X-ray photon energy levels differs from the change in X-ray absorption of calcium between the at least two different X-ray photon energy level. Embodiments of the present invention also relates to an X-ray imaging method. Embodiments of the present invention additionally relates to an image reconstruction device. Embodiments of the present invention further relates to an X-ray imaging system.

17 Claims, 4 Drawing Sheets

(51) Int. Cl.

| | |
|---|---|
| *A61B 6/40* | (2024.01) |
| *A61B 6/42* | (2024.01) |
| *A61B 6/50* | (2024.01) |
| *A61K 49/04* | (2006.01) |
| *G06T 11/00* | (2006.01) |

(52) U.S. Cl.
CPC ............ *A61B 6/5205* (2013.01); *A61K 49/04* (2013.01); *G06T 11/003* (2013.01); *G06T 2210/41* (2013.01)

(56) References Cited

U.S. PATENT DOCUMENTS

| | | |
|---|---|---|
| 2013/0261441 A1 | 10/2013 | Das et al. |
| 2018/0110492 A1* | 4/2018 | Yeh ......................... A61B 6/03 |
| 2018/0236267 A1 | 8/2018 | Kuang et al. |

FOREIGN PATENT DOCUMENTS

| | | |
|---|---|---|
| WO | WO 2016172256 A1 | 10/2016 |
| WO | WO 2017027547 A1 | 2/2017 |
| WO | WO 2017223343 A1 | 12/2017 |

* cited by examiner

CONTRAST AGENT-BASED VASCULAR IMAGING

CROSS-REFERENCE TO RELATED APPLICATION(S)

This application is the National Phase under 35 U.S.C. § 371 of International Application No. PCT/EP2020/080915, which has an international filing date of Nov. 4, 2020, and which designated the United States of America and which claims priority to German patent application number DE 102019218587.8 filed Nov. 29, 2019, the entire contents of which are incorporated herein by reference.

FIELD

At least some example embodiments of the invention relate- to an X-ray contrast agent. In addition, some example embodiments of the invention relate- to an X-ray imaging method in which said X-ray contrast agent is used. Some example embodiments of the invention also relate-a to an image reconstruction facility. Some example embodiments of the invention further relates- to an X-ray imaging system.

BACKGROUND

With the aid of modern imaging methods, two or three-dimensional image data is often created which can be used for visualizing an imaged object under investigation and also for further uses.

The imaging methods are often based upon the detection of X-ray radiation wherein so-called projection measurement data is generated. For example, projection measurement data can be acquired with the aid of a computed tomography (CT) system.

In an X-ray image recording, contrast agents are often used which are injected into the patient in order to enhance the contrast of the image recording and thereby to facilitate a diagnosis. An example for the use of contrast agents is the imaging of vessels with X-ray methods. X-ray methods can therein be carried out with conventional systems, C-arm systems, angiography systems or CT systems. Conventionally, iodine is used as the X-ray contrast agent for such an imaging method.

However, in the case of angiography with iodine, the problem arises that bones, calcifications and partially calcified plaques in the vessels have density values similar to the contrast agent-filled vessel and thus, particularly in the case of complex anatomical structures, for example in the region of the skull, iodine-filled vessels, bones and calcifications are overlaid on the vessels and can therefore no longer be precisely separated from one another in the image representation. Therefore, particularly in the case of vessels of small diameter, the width of the vessel, or lumen, can often no longer be ascertained with the aid of CT angiography in a case of severe calcification. This phenomenon represents a restriction for the use of the CT angiography for coronary arteries and peripheral leg vessels.

Conventionally, the attempt has been made, by subtraction of a pre-recording of a region to be recorded, carried out without contrast agent, to separate bones and calcifications and/or partially calcified plaques in vessels from the regions made visible by way of the iodine contrast agent. However, due to the temporal offset between the pre-recording and the main recording, problems of registration arise resulting from patient movement. Furthermore, by means of the additional image recording, the radiation dose to the patient is increased.

The use of software-based methods for separating image information relating to the vessels and image information relating to bones is also error-prone. These errors occur, in particular, in the case of complex imaging representations, for example, of the base of the skull. In addition, an elimination of (partially) calcified plaques from the representation of vessels is not possible due to the blooming effect. This is because the partially calcified plaques are represented larger than they actually are, due to the blooming effect. If the representations of the plaques are removed from the image, then, due to the excessively large areas previously covered by the plaques, regions remain for which no image information exists.

A possibility for separating bones and iodine-laden contrast agent pixels exists in the use of dual energy or multi-energy imaging methods. Therein, image recordings of one and the same examination region are carried out with at least two different mean X-ray energies. However, in simple variants in which pixels are associated with the contrast agent or the bone material by classification, similar problems arise as in the use of software-based methods. Error-prone separation of iodine-laden regions and regions having plaques also occurs, in particular with complex vascular structures. Similarly, with this procedure, an enlarged representation of calcified regions takes place. If these regions are subsequently extracted to make the vessels visible, it is unclear how the regions covered by the enlarged representation should be represented in the image.

In another relatively new method, a dual-energy image recording is used to calculate two different images on the basis of this recording, wherein one of the two images represents the structures laden with calcium and the other of the two images represents regions that are laden with contrast agent. In the contrast agent image, therefore, neither bones nor calcifications of the vessels are visible. Although, in this way, enlarged representations of the calcifications in the image are prevented and information regarding the regions otherwise covered by the enlarged structures is present, the problem still persists that previously used contrast agents such as iodine, and bones or calcifications are very similar with respect to their spectral absorption behavior in the energy range of X-ray recordings (40 keV to 140 keV). This means that for both materials, the X-ray absorption at low energies increases sharply. In FIG. 1, the absorption is represented for a recording at a low energy (labelled E(1)) and a recording at a higher energy (labelled E(2)). Due to the similar behavior of the conventional contrast agent iodine and of calcium, the resultant material images have a high level of image noise and an imprecise material separation. Although the problem of a high level of image noise and of imprecise material separation can be solved by way of a significant increase in the radiation dose, this measure entails a greater health risk to the patient and, for some examination types such as coronary angiography, cannot be realized due to technical limitations.

SUMMARY

The problem therefore exists of realizing qualitatively good vessel imaging with a low radiation dose.

This object is achieved with an X-ray contrast agent in accordance with claim 1, an X-ray imaging method in accordance with claim 5, an image reconstruction facility in accordance with claim 9 and an X-ray imaging system in accordance with claim 10.

The X-ray contrast agent according to example embodiments of the present invention has an X-ray absorption the change of which between at least two different X-ray photon energies differs significantly from the change in the X-ray absorption of calcium between the at least two different X-ray photon energies.

Ideally, the absorption by the X-ray contrast agent according to example embodiments of the present invention between the at least two different X-ray photon energies should remain almost constant. "Significantly" should be understood in this context to mean that the change amounts to less than half the change in calcium at the selected different X-ray photon energies.

Advantageously, the spectrally deviating behavior of the contrast agent according to example embodiments of the present invention can be used to represent regions which are flooded by the contrast agent separately from other image regions that are calcified or partially calcified. In particular, in the angiographic representation of vessels, more precise values for the opening width of the vessels represented and the accuracy of the representation is improved in comparison with conventionally used contrast agents. Therefore, the X-ray contrast agent according to example embodiments of the present invention can advantageously be used for the imaging representation of blood vessels, since thereby the internal diameter of vessels can be represented particularly exactly.

In the X-ray imaging method according to example embodiments of the present invention, initially a selection of a contrast agent according to the present invention takes place. Furthermore, X-ray raw data is captured from a region of an examination object which is flooded by the contrast agent with the aid of a multi-energy recording method. The X-ray imaging method according to example embodiments of the present invention can be carried out as a computer-implemented method on the basis of the captured data.

On the basis of the X-ray raw data, a material decomposition into data that is to be assigned to either the contrast agent according to example embodiments of the present invention or to calcium takes place.

Material decomposition, which is known in principle, proceeds from the consideration that an X-ray attenuation value measured by means of an X-ray image recording apparatus can be described as a linear combination of X-ray attenuation values of so-called base materials with regard to the aforementioned X-ray quantum energy distribution and/or X-ray photon energy. Measured X-ray attenuation values result from the at least two raw datasets and/or image datasets reconstructed therefrom at different X-ray quantum energy distributions. The material and/or base material in the application according to embodiments of the present invention are firstly calcium and secondly the X-ray contrast agent according to embodiments of the present invention. The X-ray attenuation of a base material dependent upon the energy of the X-ray radiation is, in principle, known or can be determined by way of prior measurements with phantoms and stored in the form of tables for retrieval in the context of the material decomposition. The result of the material decomposition is a spatial density distribution of the at least two materials, i.e. of the contrast agent according to embodiments of the present invention and of calcium in the patient, from which for each volume element in the body region of the patient that is to be imaged, the base material portions and/or the base material combination can be ascertained.

The material decomposition can both relate directly to the raw data and can also take place on the basis of the reconstructed image data. In any event, in the context of the method, at least two image datasets are generated on the basis of spectrally decomposed data, whether raw data or image data: the at least two image datasets comprise a first image dataset, which represents a first image region affected by the contrast agent according to embodiments of the present invention, and a second image dataset, which represents a second image region which is preferably complementary to the first image region in which calcium-containing structures are made visible.

In the case of a complementary representation of the first and second image dataset, regions affected by the contrast agent according to embodiments of the present invention and calcium-containing structures can be visualized together in an image, for example, by way of an overlaying of the two image datasets, wherein the relative position of the different structures and/or materials and the spatial separation and/or boundary surfaces between these different structures and/or materials are readily recognizable.

If the different materials represented by the two image datasets are present intermingled, then for separate visualization of the different materials, a separate representation of each of the first and the second image datasets in two separate images can take place.

The X-ray imaging method according to embodiments of the present invention enables a separate representation of calcium-containing image regions and those affected by the contrast agent according to embodiments of the present invention. In this way, for example, a more precise representation of the internal diameter of vessels can be achieved, which contributes to a more reliable diagnosis on the basis of angiographic image data. In addition, due to the different spectral absorption properties of the contrast agent according to embodiments of the present invention and the remaining materials to be imaged, the X-ray dose can be selected lower than with conventional imaging methods.

The image reconstruction facility according to embodiments of the present invention has an ascertaining unit for ascertaining at least two different X-ray photon energies at which a contrast agent according to embodiments of the present invention differs significantly from the change in the X-ray absorption of calcium between the at least two different X-ray photon energies.

The selection of the energy values can be taken into account in the context of a multi-energy recording method in the selection of the energies and/or mean energy values of the X-ray sources used for imaging. If counting detectors are used for capturing the X-ray radiation, then energy thresholds and/or intervals can be selected so that the aforementioned energy values are included.

Also a part of the image reconstruction facility according to embodiments of the present invention is a raw data receiving unit for receiving X-ray raw data from a region of an examination object which is at least partially flooded by the contrast agent, with the aid of a multi-energy recording method.

The image reconstruction facility according to embodiments of the present invention also comprises a decomposition unit for carrying out a material decomposition on the basis of the X-ray raw data in relation to the contrast agent and calcium and a reconstruction unit for reconstructing at least two image datasets on the basis of the material decomposition. Such material decompositions are known, in principle, for the imaging representation of a plurality of materials with the aid of dual-energy imaging or multi-energy imaging, as described above.

The at least two image datasets comprise a first image dataset which represents a first image region which is affected by the contrast agent, and a second image dataset which preferably represents a second image region which is complementary to the first image region. The image reconstruction facility according to embodiments of the present invention shares the advantages of the X-ray imaging method according to embodiments of the present invention.

The X-ray imaging system according to embodiments of the present invention has an image reconstruction unit according to embodiments of the present invention. The X-ray imaging system according to embodiments of the present invention can preferably comprise a CT angiography facility. The X-ray contrast agent according to embodiments of the present invention can advantageously be used, in particular, for the imaging representation of blood vessels, since thereby the internal diameter of vessels can be represented particularly exactly.

The essential components of the image reconstruction facility according to embodiments of the present invention can be configured mainly in the form of software components. This relates, in particular, to the decomposition unit and the reconstruction unit of the image reconstruction facility according to embodiments of the present invention. Fundamentally however, these components can also, in part, be realized in particular, if particularly rapid calculations are involved, in the form of software-supported hardware, for example, FPGAs or the like. Similarly, the required interfaces can be configured, for example, where only an acceptance of data from other software components is concerned, as software interfaces. However, they can also be configured as interfaces which are constructed as hardware and are controlled by suitable software.

A realization largely with software has the advantage that conventionally used imaging systems and/or image reconstruction facilities can also be upgraded by easy means with a software update in order to operate in the manner according to embodiments of the present invention. In this respect, the object is also achieved by means of a corresponding computer program product with a computer program which can be loaded directly into a storage facility of an X-ray imaging system, having program portions in order to carry out the steps of the X-ray imaging method according to embodiments of the present invention that can be realized with software when the program is executed in the X-ray imaging system. Such a computer program product can comprise, apart from the computer program, additional components, if relevant, such as for example, documentation and/or additional components including hardware components, for example hardware keys (dongles, etc.), in order to use the software.

For transport to the subsystem and/or for storage at or in this subsystem, a computer-readable medium, for example a memory stick, a hard disk or another transportable or firmly installed data carrier can be used on which the program portions of the computer program which can be read in and executed by a computer unit are stored. For this purpose, the computer unit can have, for example, one or more cooperating microprocessors or the like. The computer unit can be, for example, part of a terminal or a control facility of an imaging system, for example a CT system, but can also be part of a remotely arranged server system within a data transfer network which communicates with the imaging system.

The dependent claims and the description below each contain particularly advantageous embodiments and developments of the present invention. In particular, the claims of one claim category can also be further developed similarly to the dependent claims of another claim category. In addition, in the context of the present invention, the different features of different example embodiments and claims can also be combined to form new example embodiments.

In a variant of the X-ray contrast agent according to embodiments of the present invention, the X-ray absorption of the X-ray contrast agent for the at least two X-ray photon energies is not significantly different. Advantageously, the X-ray contrast agent according to embodiments of the present invention therefore differs with regard to its absorption behavior dependent upon the photon energy as compared with materials occurring, in particular, in angiography, such as calcium.

It is particularly advantageous if the spectrum of the X-ray absorption of the X-ray contrast agent according to embodiments of the present invention is similar to the spectrum of the X-ray absorption of water or soft tissue. The reason is that water or soft tissue exhibit a behavior in an energy range that is relevant for angiography which is independent of the X-ray photon energy and can therefore easily be separated from other body materials, such as for example, calcium.

In a particularly advantageous embodiment of the present invention, the X-ray contrast agent according to embodiments of the present invention has one of the following materials:

tungsten, tantalum, hafnium, gold.

The materials mentioned all advantageously have an absorption behavior similar to water and can therefore easily be separated or represented separately from calcium-containing materials of an examination region.

In one embodiment of the X-ray imaging method according to the present invention, it has a multi-energy imaging method, preferably a dual-energy imaging method. In the multi-energy imaging method, at least two different X-ray tube voltages are specified at which the change in the X-ray absorption of the contrast agent according to embodiments of the present invention significantly differs from the X-ray absorption of calcium. Furthermore, at least two X-ray image recordings are carried out with the at least two different X-ray tube voltages for acquisition of a first raw dataset and at least one second raw data set. The material decomposition then takes place on the basis of the at least two raw datasets. In this variant, with the aid of different X-ray tube voltages, X-rays with different X-ray spectra are generated, which are used for generating at least two raw datasets which are used for separating different materials during the imaging.

In an alternative embodiment of the X-ray imaging method according to embodiments of the present invention, X-ray raw data which has been recorded with the aid of a photon-counting detector in an energy-resolved manner is captured, wherein the energy thresholds of the photon-counting detector are set such that in the different energy ranges specified by way of the energy thresholds, the change in the X-ray absorption of the contrast agent according to embodiments of the present invention differs significantly from the change in the X-ray absorption of calcium. Furthermore, a material decomposition takes place on the basis of the energy-resolved raw data. Advantageously, in this variant, only the irradiation of an examination region with just one X-ray tube is needed.

BRIEF DESCRIPTION OF THE DRAWINGS

The present invention will now be described again in greater detail using example embodiments, making reference to the accompanying drawings. In the drawings:

FIG. 5 shows a schematic representation of an image reconstruction facility according to an example embodiment of the present invention.

DETAILED DESCRIPTION

Figure 1:
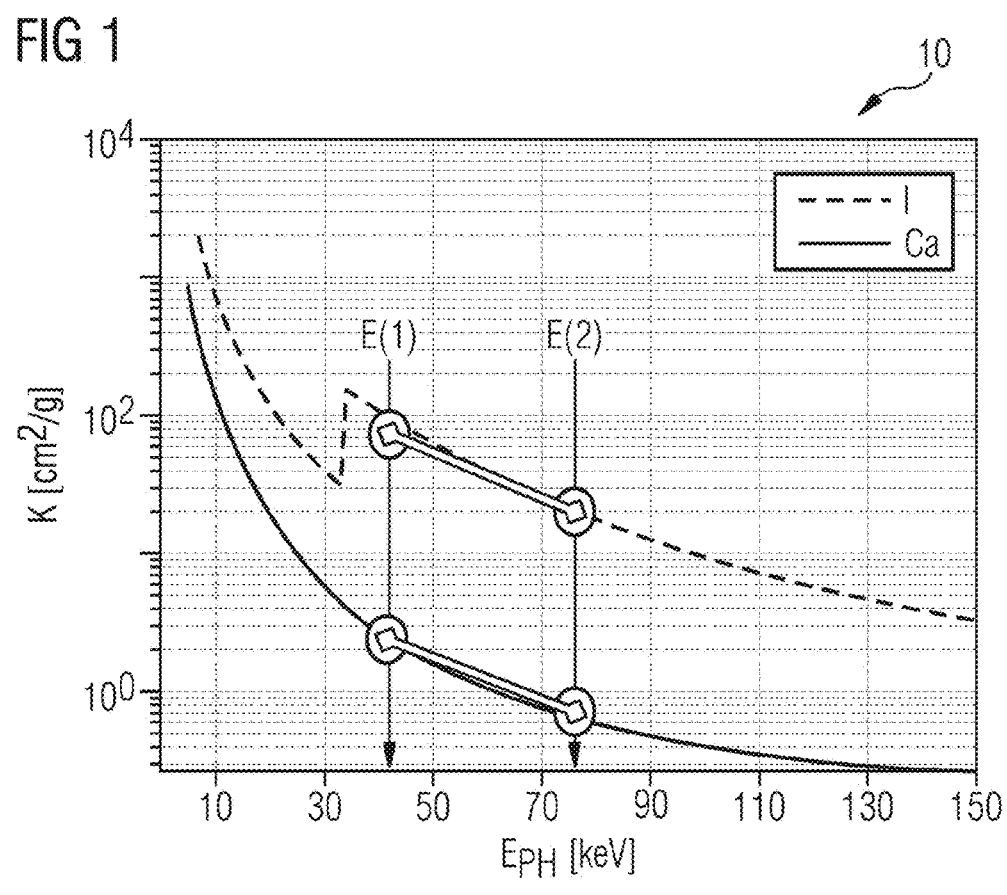
FIG. 1 shows a graphical representation that illustrates the absorption properties of the contrast agent iodine and the bone material calcium dependent upon the energy of the X-ray photons.

FIG. 1 shows a graphical representation 10 that illustrates the absorption properties of the contrast agent iodine I and of the bone material calcium Ca dependent upon the energy EPH of the X-ray photons. For the visualization of the absorption of the materials mentioned, the mass absorption coefficient K is shown dependent upon the energy EPH of the X-ray photons. Furthermore, in FIG. 1, a typical mean energy E(1) of an image recording with a low energy and the mean energy E(2) of an image recording with the high energy of a dual-energy image recording is shown. As shown in FIG. 1, the progression of the two curves of the mass absorption coefficient of iodine I and of calcium Ca is very similar. It must therein be taken into account that the materials iodine and calcium can be present in different densities and concentrations. This has the result that, in the most unfavorable case, the absorption curves shown in FIG. 1 overlap one another completely. A pictorial separation of the two materials is then no longer possible.

Figure 2:
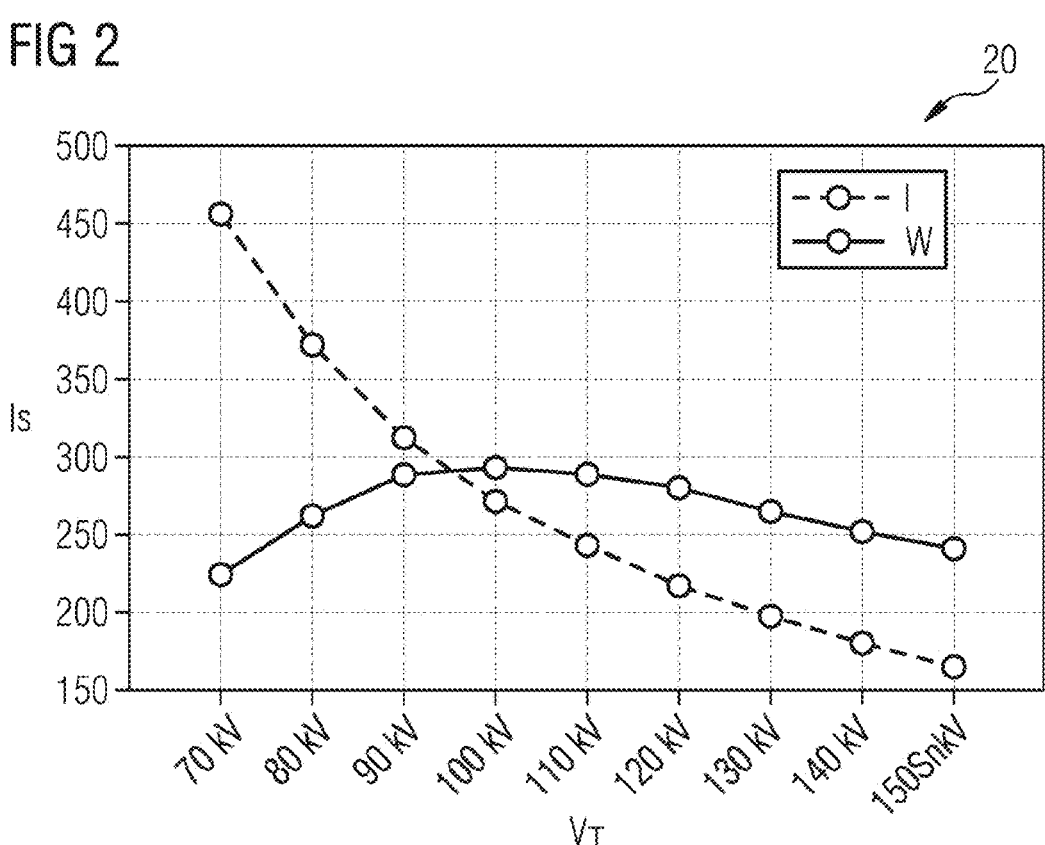
FIG. 2 shows a graphical representation that illustrates absorption values of the contrast agent iodine and the material tungsten dependent upon the tube voltage of an X-ray device.

FIG. 2 shows a graphical representation 20 that illustrates absorption values Is of the contrast agent iodine I and the material tungsten W dependent upon the tube voltage VT of an X-ray device. Whereas the X-ray absorption of iodine decreases with increasing energy, the X-ray absorption of tungsten W decreases only slightly with increasing energy.

Particularly in a dual-energy image recording at a low energy of 80 kV and a higher energy of 140 kV or 150 kV with a tin filter, the X-ray absorption Is of tungsten W changes practically not at all as compared with the X-ray absorption of iodine. Therefore, image points at which the two individual recordings are generated with different tube voltages can easily be associated with one of the two contrast agents. For example, a point at which the absorption is the same in the two images is clearly attributable to the material tungsten and a point at which the absorption in the two images is strongly different is clearly attributable to the material iodine.

Figure 3:
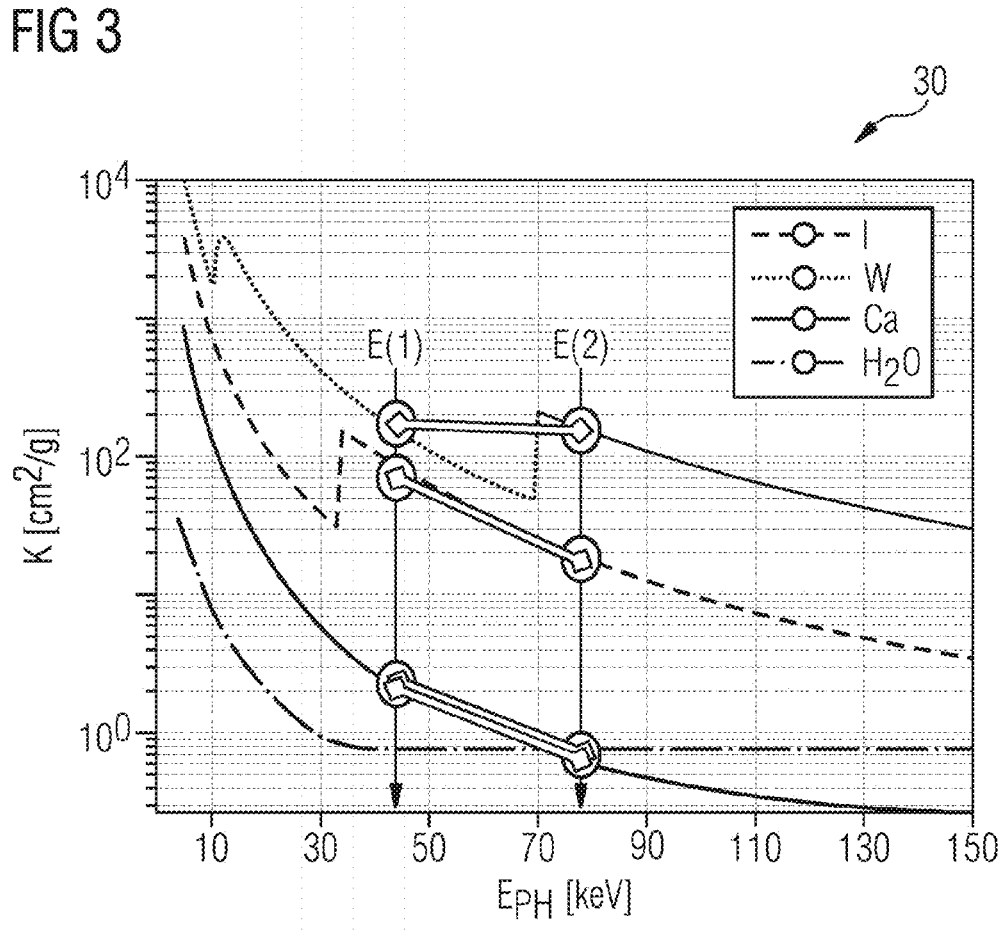
FIG. 3 shows a graphical representation that illustrates the absorption properties of the contrast agent iodine and of calcium and water dependent upon the energy of the X-ray photons.

FIG. 3 shows a graphical representation 30 that illustrates the absorption properties of the contrast agents iodine I and tungsten W as well as those of calcium Ca and water H2O, dependent upon the energy EPH of the X-ray photons. For each of the materials mentioned, the mass absorption coefficient K is shown dependent upon the energy EPH of the X-ray photons. It is clearly apparent in FIG. 3 that the absorption of the contrast agent iodine I and of the bone material calcium Ca decreases greatly in the region from 40 to 80 keV with increasing photon energy EPH. It should be noted that therein the absorption is shown logarithmically. In contrast thereto, tungsten W behaves more like water H2O. That is, the absorption of tungsten W for a first photon energy E(1), which is at approximately 45 keV, is equal to the absorption at a second photon energy E(2) which is at approximately 80 keV. Due to the strongly differing behavior of tungsten W as compared with calcium Ca, image regions which are laden with tungsten W can readily be separated or separately represented from regions in which calcium Ca prevails.

Figure 4:
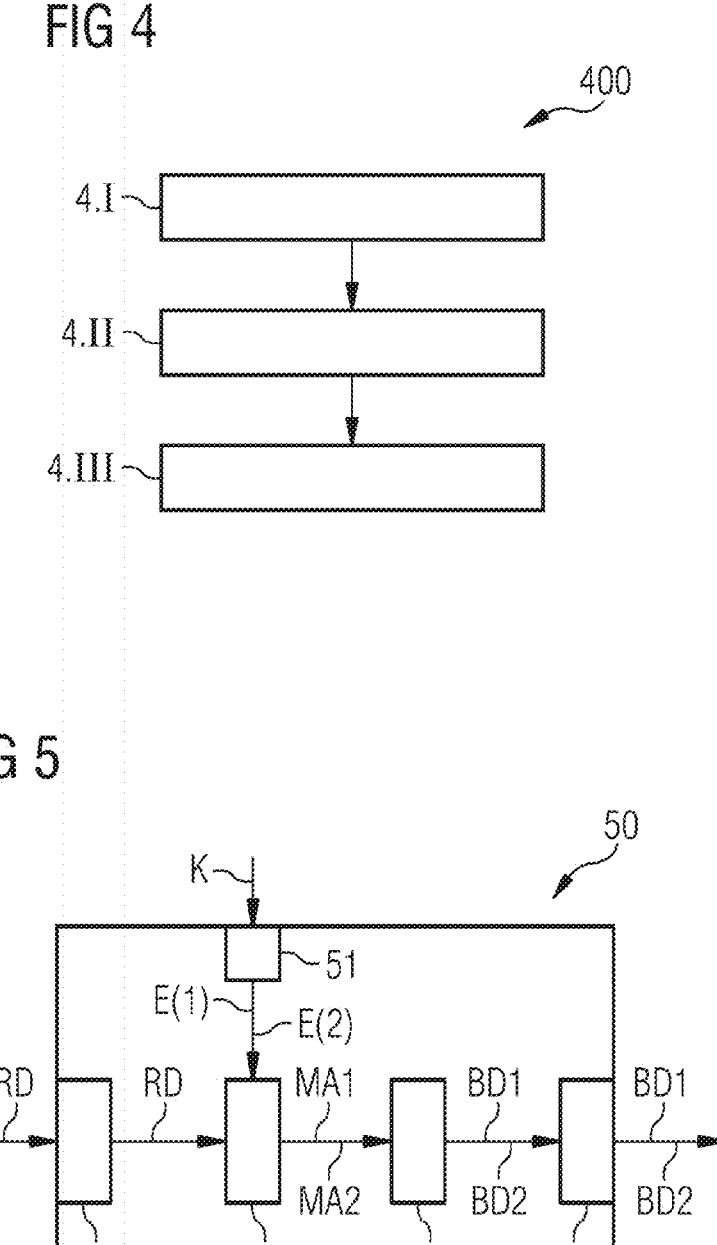
FIG. 4 shows a flow diagram that illustrates an X-ray imaging method according to an example embodiment of the present invention.

FIG. 4 shows a flow diagram 400 which illustrates an X-ray imaging method according to an example embodiment of the present invention. In the step 4.I, initially a contrast agent based upon the element tungsten is selected for an angiographic imaging of an examination region of a patient, for example, the skull of the patient. Furthermore, in the step 4.II, X-ray raw data RD that has been recorded from a region of an examination object O which is flooded with the selected contrast agent with the aid of a dual-energy recording method is captured. In the method visualized in FIG. 4, X-ray raw data that has been recorded with X-rays at two different energy values E(1) and E(2) is captured. The energy values are therein selected such that the absorption behavior of the selected contrast agent based upon the material tungsten is the same for both the energy values in this example embodiment. This process can be realized, for example, by way of the use of two detectors arranged spatially separated from one another, wherein a filter is introduced into the beam path in front of one of the two detectors, said filter filtering out part of the spectrum of the X-rays. Thus, two raw datasets to which different X-ray energies E(1) and E(2) are assigned are captured.

In step 4.III, a reconstruction of two image datasets BD1, BD2 takes place on the basis of the two raw datasets generated in step 4.II. Therein a first image dataset BD1 is generated which represents a first image region affected by the contrast agent tungsten, and a second image dataset BD2 is generated which represents a second image region, which is complementary to the first image region, and in which calcium-based structures are made visible. The creation of the two image datasets BD1, BD2 can take place, for example, with the aid of a material decomposition on the basis of the raw data acquired in step 4.II.

FIG. 5 shows a reconstruction facility 50. The reconstruction facility 50 has an ascertaining unit 51. The ascertaining unit 51 receives information regarding the contrast agent K to be used and establishes values E(1), E(2) of two different X-ray photon energies at which a selected contrast agent K behaves like water, i.e. the absorption is the same for both energy values. However, the image regions laden with calcium that are to be separated from the contrast agent K have, in energy regions that can be used by X-ray devices, a clear spectral dependence of the absorption and can therefore easily be differentiated at the established energy values E(1), E(2) from the selected contrast agent K. The selection of the energy values E(1), E(2) can take place, for example, on the basis of energy-dependent absorption values of the selected contrast agent K stored in a data store.

The selection of the energy values E(1), E(2) can be taken into account, in the context of a multi-energy recording method, in the selection of the energies and/or mean energy values of the X-ray sources used for imaging. If counting detectors are used for capturing the X-ray radiation, then energy thresholds and/or intervals can be selected so that the energy values mentioned are included.

The reconstruction facility 50 also has a raw data receiving unit 52 for receiving X-ray raw data RD. The raw data RD has been acquired with the aid of a dual-energy CT method from a region of an examination object which is partially flooded by the contrast agent K.

The raw data RD is passed on to a decomposition unit 53 which carries out a material decomposition of the raw data RD on the basis of the X-ray raw data RD in relation to the contrast agent K and calcium. The material-specific portions MA1, MA2 of the raw data which are associated with the individual absorption spectra of the different materials are transferred to the reconstruction unit 54 which reconstructs at least two image datasets BD1, BD2 on the basis of the material-specific portions MA1, MA2. A first image dataset BD1 visualizes a first image region affected by the contrast agent and a second image dataset BD2 visualizes a second image region which is complementary to the first image region, and in which structures laden with calcium or structures contrasted with iodine prevail. The image datasets BD1, BD2 generated are output by means of an output interface 55, for example, to a display unit, a data storage unit or a control computer with an image display.

Figure 6:
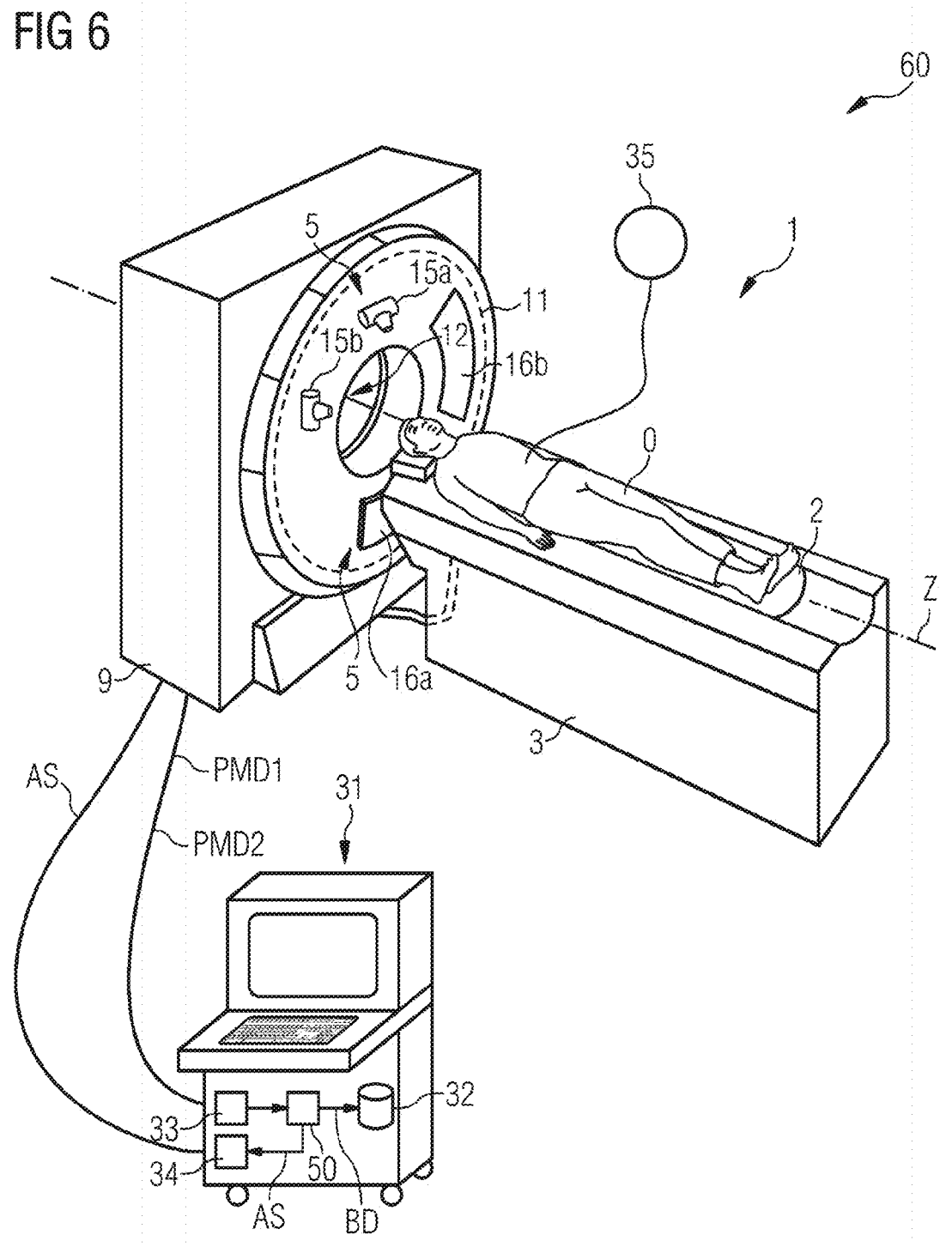
FIG. 6 shows a schematic representation of a CT system according to an example embodiment of the present invention.

FIG. 6 shows an X-ray imaging system, in this case a CT system 60, according to an example embodiment of the present invention.

The CT system 60 which is configured as a dual-energy CT system, substantially consists therein of a typical scanner 9 in which a projection measurement data acquisition unit 5 with two detectors 16*a*, 16*b* and two X-ray sources 15*a*, 15*b* arranged opposite the two detectors 16*a*, 16*b* circulates on a gantry 11 round a measurement space 12. Situated in front of the scanner 9 is a patient positioning apparatus 3 and/or a patient table 3, the upper part 2 of which can be displaced with a patient O situated thereon toward the scanner 9, in order to move the patient O through the measurement space 12 relative to the detector system 16*a*, 16*b*. The scanner 9 and the patient table 3 are controlled by way of a control facility 31 from which acquisition control signals AS come via a conventional control interface 34 in order to control the whole system in the conventional manner according to predetermined scan protocols. In the case of a spiral acquisition, by way of a movement of the patient O along the z-direction which corresponds to the system axis z through the measurement space 12 and the simultaneous circulation of the X-ray sources 15*a*, 15*b*, for the X-ray sources 15*a*, 15*b* relative to the patient O during the scan, a helical path results. The detectors 16*a*, 16*b* therein always move in parallel relative to the X-ray sources 15*a*, 15*b*, in order to capture projection measurement data PMD1, PMD2 which is then used for the reconstruction of volume and/or slice image data. Similarly, a sequential scanning method can also be carried out in which a fixed position in the z-direction is approached and then, during a circulation, a partial circulation or a plurality of circulations at the z-position in question, the required projection measurement data PMD1, PMD2 is captured, in order to reconstruct a sectional image at this z-position or to reconstruct image data from the projection measurement data of a plurality of z-positions. The method according to embodiments of the present invention can also in principle be used with other CT systems, for example, with just one X-ray source or with a detector forming a complete ring. For example, the inventive method can also be used on a system with an unmoved patient table and a gantry moved in the z-direction (a so-called sliding gantry).

The projection measurement data PMD1, PMD2 (also referred to here as raw data) acquired from the detectors 16*a*, 16*b* is transferred via a raw data interface 33 to the control facility 31. This raw data is then further processed, possibly after a suitable pre-processing in a reconstruction facility 50 which, in this example embodiment, is realized in the control facility 31 in the form of software on a processor. This reconstruction facility 50 reconstructs, on the basis of the raw data PMD1, PMD2, two image datasets BD1, BD2 of which a first image dataset BD1 visualizes vessel structures affected by a contrast agent K according to embodiments of the present invention and a second image dataset BD2 visualizes bone structures and calcified or partially calcified regions in the vessels.

The exact configuration of such a reconstruction facility 50 is illustrated in detail in FIG. 5.

The image data BD1, BD2 generated by the reconstruction facility 50 is then stored in a memory store 32 of the control facility 31 and/or is output in the usual manner on the screen of the control facility 31. Thus, by means of an interface (not shown in FIG. 6), it can also be fed into a network connected to the computed tomography system 60, for example, a radiological information system (RIS), and stored in a mass memory store accessible there or output as images to printers or filming stations connected there. The data can thus be further processed in any desired manner and then stored or output.

In addition in FIG. 6, a contrast agent injection facility 35 is shown, with which a contrast agent K is injected into the patient O in advance, that is before the start of the CT imaging method. The regions which are flooded by the contrast agent K and bone structures and (partially) calcified regions can then be captured in image form with the aid of the computed tomography system 60 using the X-ray imaging method according to embodiments of the present invention.

The components of the reconstruction facility 50 can be realized mainly or entirely in the form of software elements on a suitable processor. In particular, the interfaces between these components can also be configured purely as software. It is required only that access possibilities exist in suitable memory storage regions in which the data can be suitably placed in intermediate storage and called up again and updated at any time.

Finally, it should again be noted that the methods and apparatuses described above are merely preferred example embodiments of the present invention and that embodiments of the present invention can also be modified by a person skilled in the art without departing from the field of the present invention, to the extent that it is specified by the claims. For the sake of completeness, it should also be mentioned that the use of the indefinite article "a" or "an" does not preclude the relevant features from being present plurally. Similarly, the expression "unit" does not preclude this consisting of a plurality of components which can possibly also be spatially distributed.

The invention claimed is:

1. An X-ray contrast agent including, at least one selected material having a first X-ray absorption that is different from a second X-ray absorption of calcium, to cause a visual difference on a resulting image between the X-ray contrast agent and calcium when subjected to at least two different X-ray photon energies.

2. The X-ray contrast agent of claim 1, wherein the X-ray absorption of the X-ray contrast agent for the at least two different X-ray photon energies is not significantly different.

3. The X-ray contrast agent of claim 1, wherein a spectrum of the X-ray absorption of the X-ray contrast agent is similar to a spectrum of the X-ray absorption of water or soft tissue.

4. The X-ray contrast agent of claim 1, wherein the at least one selected material has at least one of the following materials:

tungsten, tantalum, hafnium, or gold.

5. An X-ray imaging method, comprising:

selecting the X-ray contrast agent of claim 1, capturing X-ray raw data from a region of an examination object using a multi-energy recording method, the region of the examination object including the X-ray contrast agent, carrying out a material decomposition based on the X-ray raw data in relation to the X-ray contrast agent and calcium, and reconstructing at least two image datasets based on the material decomposition, the at least two image datasets including, a first image dataset representing a first image region defined by an area subjected to the X-ray contrast agent, and a second image dataset representing a second image region, the second image region including at least one calcified structure and being complementary to the first image region.

6. The X-ray imaging method of claim 5, further comprising:

a multi-energy imaging method including, specifying at least two different X-ray tube voltages at which a change in the X-ray absorption of the X-ray contrast agent significantly differs from calcium, capturing at least two datasets of X-ray image recordings that have been recorded with the at least two different X-ray tube voltages for acquisition of a first raw dataset and at least one second raw dataset, and carrying out the material decomposition based on the first raw dataset and the at least one second raw dataset.

7. The X-ray imaging method of claim 5, further comprising:

capturing X-ray raw data using a photon-counting detector in an energy-resolved manner, wherein energy thresholds of the photon-counting detector are set such that therewith, a change in the X-ray absorption of the X-ray contrast agent differs from the change in the X-ray absorption of calcium, carrying out the material decomposition based on the X-ray raw data.

8. The X-ray imaging method of claim 5, further comprising:

a CT angiographic imaging method.

9. An image reconstruction facility, having:

a memory configured to store instructions; and a processor configured to execute the instructions to cause the image reconstruction facility to ascertain at least two different X-ray photon energies at which the X-ray contrast agent of claim 1 differs significantly from a change in the X-ray absorption of calcium between the at least two different X-ray photon energies, receive X-ray raw data from a region of an examination object which is partially flooded by the X-ray contrast agent via a multi-energy recording method, carry out a material decomposition based on the X-ray raw data in relation to the X-ray contrast agent and calcium, and reconstruct at least two image datasets based on the material decomposition, the at least two image datasets including, a first image dataset representing a first image region affected by the X-ray contrast agent, and a second image dataset representing a second image region, the second image region being complementary to the first image region.

10. An X-ray imaging system, having the image reconstruction facility of claim 9.

11. The X-ray imaging system of claim 10, having a CT angiography facility.

12. A computer program product having a computer program, when executed by a storage facility of an X-ray imaging system, cause the X-ray imaging system to perform the method of claim 5.

13. A non-transitory computer-readable medium on which program portions that can be read in and executed by a computer unit are stored, is configured to cause the computer unit to perform the method of claim 5.

14. The X-ray contrast agent of claim 2, wherein a spectrum of the X-ray absorption of the X-ray contrast agent is similar to a spectrum of the X-ray absorption of water or soft tissue.

15. The X-ray contrast agent of claim 2, wherein the at least one selected material has at least one of the following materials:

tungsten, tantalum, hafnium, or gold.

16. The X-ray contrast agent of claim 3, wherein the at least one selected material has at least one of the following materials:

tungsten, tantalum, hafnium, or gold.

17. The X-ray contrast agent of claim 1, wherein the X-ray absorption for the X-ray contrast agent for the at least two different X-ray photon energies is less than half a change in the X-ray absorption of calcium for the at least two different X-ray photon energies.

* * * * *